(12) United States Patent
Lin et al.

(10) Patent No.: US 7,486,980 B2
(45) Date of Patent: Feb. 3, 2009

(54) BIO-MONITORING APPARATUS

(75) Inventors: Wen-Shan Lin, Kaohsiung (TW); Ting-Chen Ke, Taichung (TW); Wen-Ying Chang, Tainan County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 84 days.

(21) Appl. No.: 11/567,843

(22) Filed: Dec. 7, 2006

(65) Prior Publication Data

US 2008/0108889 A1    May 8, 2008

(30) Foreign Application Priority Data

Nov. 8, 2006   (TW) .............................. 95141265 A

(51) Int. Cl.
*A61B 5/04* (2006.01)
(52) U.S. Cl. ...................................... 600/391; 600/393
(58) Field of Classification Search ................. 600/382, 600/386, 391–393
See application file for complete search history.

(56) References Cited

U.S. PATENT DOCUMENTS

| | | | | |
|---|---|---|---|---|
| 4,051,842 A | * | 10/1977 | Hazel et al. | 600/391 |
| 4,353,372 A | * | 10/1982 | Ayer | 600/393 |
| 4,398,545 A | * | 8/1983 | Wilson | 607/152 |
| 4,669,479 A | * | 6/1987 | Dunseath, Jr. | 600/391 |
| H516 H | * | 9/1988 | Lattin et al. | 604/20 |
| 5,622,168 A | | 4/1997 | Keusch et al. | |
| 5,634,468 A | * | 6/1997 | Platt et al. | 600/509 |
| 6,643,541 B2 | * | 11/2003 | Mok et al. | 600/546 |
| 2007/0093705 A1 | * | 4/2007 | Shin et al. | 600/372 |

FOREIGN PATENT DOCUMENTS

TW         091205932       3/2004

* cited by examiner

*Primary Examiner*—Lee S Cohen
(74) *Attorney, Agent, or Firm*—WPAT., P.C.; Justin King

(57) ABSTRACT

A bio-monitoring apparatus is disclosed in the present invention which is characterized in that a bio-sensing electrode without a stud member or male portion of a snap fastener is directly integrated with a signal processing module through a conductive layer formed therebetween so as to form the bio-monitoring apparatus functions to transcutaneously sense physiological statuses of a being. In a preferred embodiment of the present invention, the structure of the bio-sensing electrode is further simplified to a contacting layer coupled to the signal processing module through the conductive layer so as to reduce attenuation of signal intensity during signal transmitting. Meanwhile, without the stud member disposed in the electrode, not only the thickness of the electrode is certainly reduced, but also the feeling of comfort is capable of being improved while the electrode is adapted to contact a being.

7 Claims, 5 Drawing Sheets

BIO-MONITORING APPARATUS

FIELD OF THE INVENTION

The present invention relates to a bio-monitoring apparatus, and more particularly, to a apparatus for monitoring human physical attributes that is achieved by integrating a conventional biosensor with a processing module while eliminating any metal stud required in the conventional biosensor, and thereby, not only the thickness of the bio-monitoring apparatus is certainly reduced, but also the comfort of a person being monitored and attached thereby is improved.

BACKGROUND OF THE INVENTION

With rapid advance of medical technology that help to improve the life expectancy of every human population, researches relating to apparatus capable of sensing and monitoring physiological signals are becoming popular as health management and disease prevention are becoming an important issue of our everyday life. Hence, various sensing apparatus for monitoring physiological attributes, no matter it is a medical-grade device specialized for hospitals or is a homecare device for daily usage, are being developed.

Among those sensible physiological attributes, data acquired from electrocardiogram (ECG) might be the essential one, which is a graphic produced by an electrocardiograph and recording the electrical voltage in the heart in the form of a continuous strip graph. It is the prime tool in cardiac electrophysiology, and has a prime function in the screening and diagnosis of cardiovascular diseases, such as detecting potassium, calcium, magnesium and other electrolyte disturbances, determining whether the heart is performing normally or suffering from abnormalities (eg. extra slow heartbeats—bradycardia), etc.

Most electrode patches used in currently available electrocardiographs are substantially sensing units that can be attached to skin for sensing electrical information and are designed and structured separated from the electrocardiographs, i.e. each of those conventional electrode patches is electrically connected to an electrocardiograph only by connecting a signal wire extending from each electrode patch to the electrocardiograph. However, the task of connecting and wiring electrode patches to an electrocardiograph is pretty complicated and troublesome, which causes great inconvenience for person operating the electrocardiograph.

It is noted that most conventional electrode patches are composed as a paster-type patch with metal stud fitted thereon, such as those disclosed in TW Pat. No. 00581319 and U.S. Pat. No. 5,622,168. Please refer to FIG. 1A and FIG. 1B, which shows respectively an electrode patch disclosed in TW Pat. No. 00581319 and another electrode patch disclosed in U.S. Pat. No. 5,622,168. However, the arranging of a metal stud 1 on an electrode patch not only will increase the thickness of the resulting electrode patch, but also it will cause discomfort to any person attached thereby.

Therefore, it is in need of an improved bio-monitoring apparatus that is freed from those shortcomings of prior arts.

SUMMARY OF THE INVENTION

It is the primary object of the present invention to provide to a apparatus for monitoring human physical attributes that is achieved by integrating a thin electrode patch with a processing module while eliminating any metal stud required in conventional electrode patches for enabling the same to be attached directly to a specific position of a human body without requiring any wiring as those conventional electrode patches did.

It is another object of the invention to provide a bio-monitoring apparatus, being a simple integrated device of a studless electrode patch and a processing module, by which the stud conventionally required for connecting the electrode patch with the processing module can be eliminated so as to reduce the thickness of the resulting electrode patch and thus reduce the amount of electrically connections required to be enabled inside the bio-monitoring apparatus between the components thereof so as to reduce the cost of manufacturing the same.

Yet, another object of the invention is to provide a bio-sensing apparatus, being a simple integrated device of a studless electrode patch and a processing module, by which the attenuation of signal intensity during signal transmitting can be reduced as the path of signal transmission is shortened.

Furthermore, another object of the invention is to provide a bio-sensing apparatus having electrode patches without metal studs formed thereon, that is capable of improving the comfort of a being as one is being monitored thereby.

To achieve the above objects, the present invention provides a bio-monitoring apparatus, comprising: a signal processing module; at least an electrode patch, each disposed on the signal processing module while being enabled to sensing a bio signal; and at least a conductive layer, each being formed and sandwiched between the at least one electrode patch and the signal processing module for enabling an electrical connection between the at least one electrode patch and the signal processing module and thus transmitting the bio signal to the signal processing module.

Preferably, each electrode patch is further comprised of: an electrode, having a via hole formed thereon; and at least a contact layer, capable of connecting electrically to the conductive layer through the via hole. In addition, a layer of a conductive material is formed on the electrode at a position sandwiched between the contact layer and the electrode for enabling the contact layer to electrically connected to the electrode. In a preferred aspect, the conductive material can be a material selected from the group consisting of a conductive adhesive, a conductive paste and the combinations thereof; and the electrode can be an object selected from the group consisting of a self-adhesive conductive paster, a silicon rubber conductive sheet, an aluminum conductive sheet and the combinations thereof.

Preferably, the conductive layer is made of a material selected from the group consisting of a gold soldering pad, a copper foil, a carbon skin, and the combinations thereof.

Preferably, the signal processing module is further comprised of: a flexible substrate; and at least a processing circuit, formed on the flexible substrate for processing the bio signal.

Preferably, the bio-monitoring apparatus further comprises: a power module, for providing power to the signal processing module.

In a preferred embodiment of the invention, the present invention provide a bio-monitoring apparatus, comprising: a signal processing module; at least a contact layer, disposed on the signal processing module while being enabled to sensing a bio signal; and at least a conductive layer, each being formed and sandwiched between the at least one contact layer and the signal processing module for enabling the signal processing module to electrically connect to the at least one contact layer and thus enabling the bio signal to be transmitted to the signal processing module.

Other aspects and advantages of the present invention will become apparent from the following detailed description, taken in conjunction with the accompanying drawings, illustrating by way of example the principles of the present invention.

DESCRIPTION OF THE PREFERRED EMBODIMENT

For your esteemed members of reviewing committee to further understand and recognize the fulfilled functions and structural characteristics of the invention, several preferable embodiments cooperating with detailed description are presented as the follows.

Figure 1A:
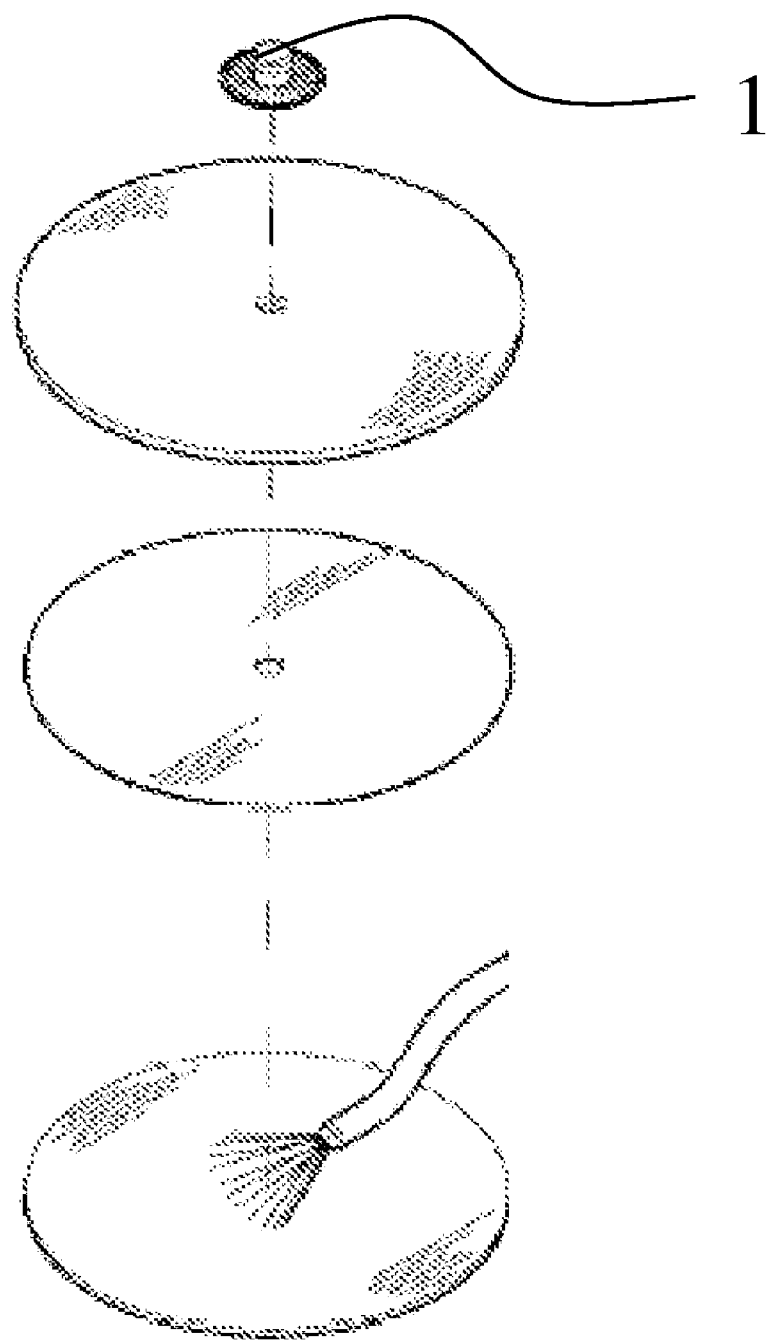
FIG. 1A shows an electrode patch disclosed in TW Pat. No. 00581319.
Figure 1B:
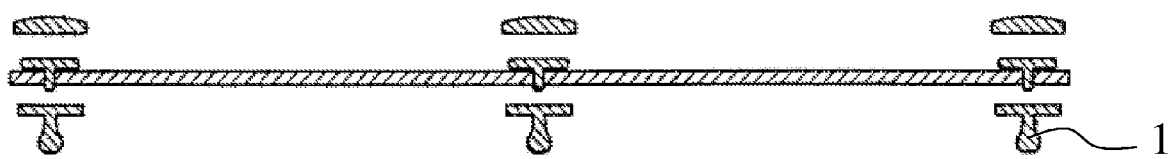
FIG. 1B shows an electrode patch disclosed in U.S. Pat. No. 5,622,168.
Figure 2A:
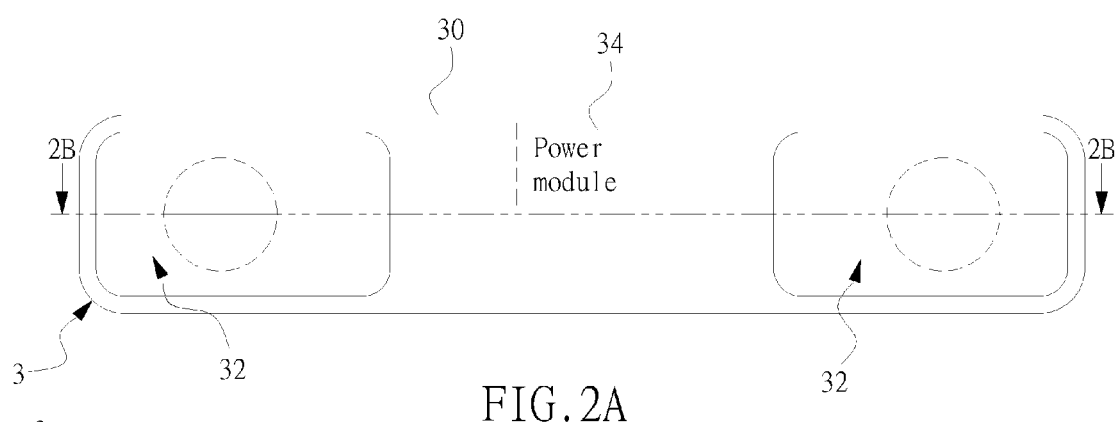
FIG. 2A is a top view of a bio-monitoring apparatus according to a preferred embodiment of the invention.
Figure 2B:
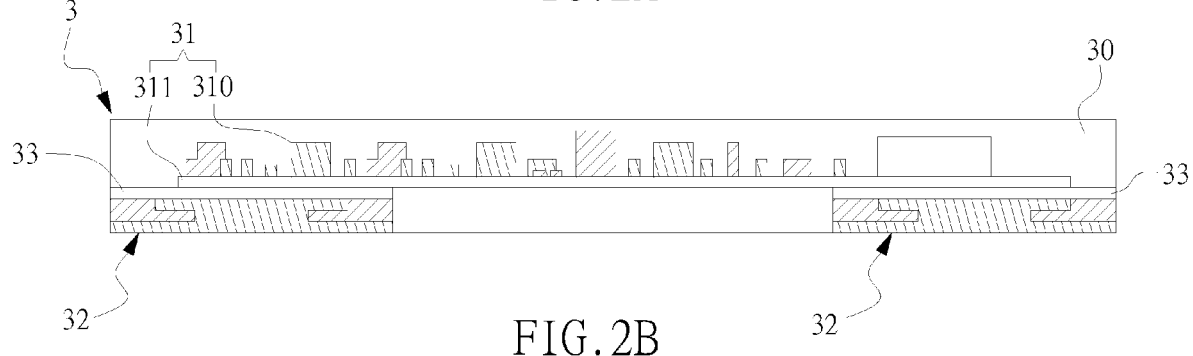
FIG. 2B is a cross-sectional view of FIG. 2A.

Please refer to FIG. 2A and FIG. 2B, which are respectively a top view and a cross-sectional view of a bio-monitoring apparatus according to a preferred embodiment of the invention. The bio-monitoring apparatus 3 is comprised of: a signal processing module 31; and at least an electrode patch 32, each coupled to the processing circuit 31 by a conductive layer 33. In which, the signal processing module 31 is further composed of: a flexible substrate 311, and a processing circuit 310 coupled to the flexible substrate 311. As the signal processing module 31 is basically a processing circuit 310 formed on a flexible substrate 311, it is considered to be flexible that can be bended for closely adhering the same to a test area. In a preferred aspect, the whole signal processing module 31 comprising the processing circuit 310 and the flexible substrate 311 is packed inside a package structure 30 for protecting the processing circuit 310 and the flexible substrate 311. Moreover, the bio-monitoring apparatus 3 further comprises a power module 34, which can be a lithium (Li) battery, a rechargeable battery or other external power source. It is noted that the amount of the electrode patch 32 is dependent upon actual requirement of a test performing on a being and thus is not limited by those illustrated in the embodiment shown in FIG. 2A and FIG. 2B.

Furthermore, the conductive layer 33 can be a gold soldering pad, a copper foil, a carbon skin, and the combinations thereof, but is not limited thereby. The purpose of the conductive layer 33 is to enable the electrode patch 32 to connect electrically to the signal processing module 31 and thus enable signals sensed by the electrode patch 32 to be transmitted to the signal processing module 31 smoothly.

Figure 3A:
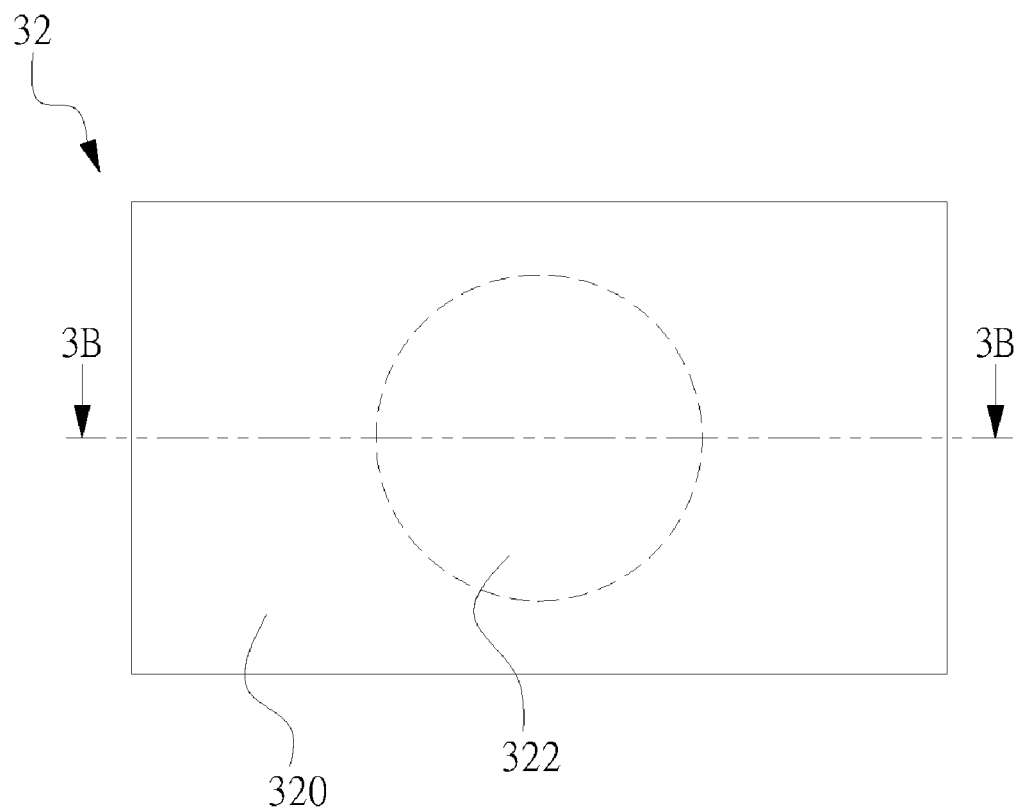
FIG. 3A is a top view of an electrode patch according to a preferred embodiment of the invention.
Figure 3B:
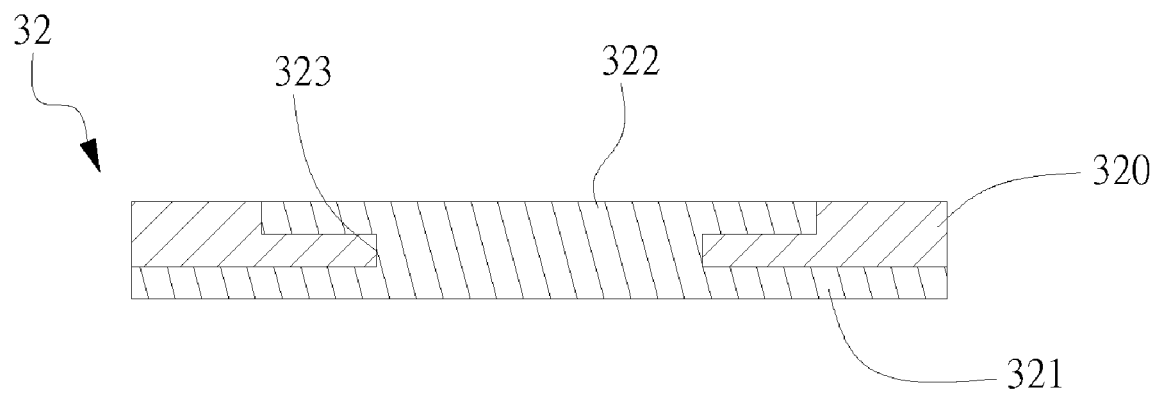
FIG. 3B is a cross-sectional view of FIG. 3A.

Please refer to FIG. 3A and FIG. 3B, which are respectively a top view and a cross-sectional view of an electrode patch according to a preferred embodiment of the invention. The electrode patch 32 is further comprised of: an electrode 320, having a via hole 323 formed thereon; and a contact layer 321, disposed at a side of the electrode 320 that is to be contacted with a test area of a being, capable of connecting electrically to the conductive layer 33 through the via hole 323. In addition, a layer of a conductive material, referring as a conductive material layer 322, is formed on the electrode 320 at a side thereof proximate to the conductive layer 33, which is further electrically connected to the conductive layer 33 for enabling signal transmission therebetween.

In this preferred embodiment, the electrode 320 can be an object selected from the group consisting of a self-adhesive conductive paste, a silicon rubber conductive sheet, an aluminum conductive sheet and the combinations thereof; and the contact layer 321 can be made of a material selected from the group consisting of a conductive adhesive, a conductive paste and the combinations thereof, by which the intensity and quality of signals sensed thereby can be enhanced. Moreover, the conductive material composing the conductive material layer 322 can also be a material selected from the group consisting of a conductive adhesive, a conductive paste and the combinations thereof.

Figure 4:
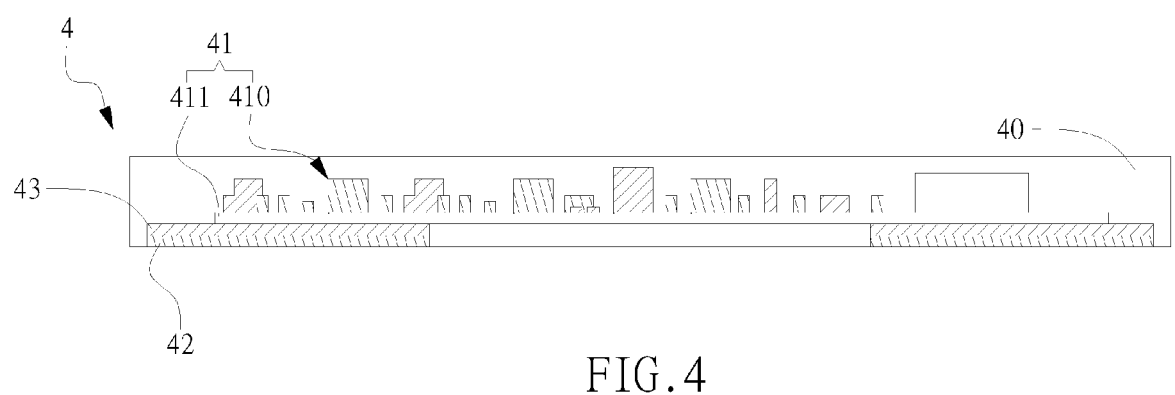
FIG. 4 is a cross-sectional view of a bio-monitoring apparatus according to another preferred embodiment of the invention.

Please refer to FIG. 4, which is a cross-sectional view of a bio-monitoring apparatus according to another preferred embodiment of the invention. The bio-monitoring apparatus 4 is comprised of: a signal processing module 41; at least a contact layer 42, disposed on the signal processing module 41 while being enabled to sensing a bio signal; and at least a conductive layer 43, each being formed and sandwiched between the at least one contact layer 42 and the signal processing module 41 for enabling the signal processing module 41 to electrically connect to the at least one contact layer 42 and thus enabling the bio signal to be transmitted to the signal processing module 41. Preferably, each contact layer 42 can be made of a material selected from the group consisting of a conductive adhesive, a conductive paste and the combinations thereof.

Moreover, the signal processing module 41 is further composed of: a flexible substrate 411, and a processing circuit 410 coupled to the flexible substrate 411; and as the signal processing module 41 is basically a processing circuit 410 formed on a flexible substrate 411, it is considered to be flexible that can be bended for closely adhering the same to a test area. In a preferred aspect, the whole signal processing module 41 comprising the processing circuit 410 and the flexible substrate 411 is packed inside a package structure 40 for protecting the processing circuit 410 and the flexible substrate 411. Moreover, the bio-monitoring apparatus 4 further comprises a power module, which can be a lithium (Li) battery, a rechargeable battery or other external power source. It is noted that although there are only two contact layers 42 being shown in the embodiment of FIG. 4, the amount of the contact layer 42 is dependent upon actual requirement of a test performing on a being and thus is not limited by those illustrated in the embodiment shown in FIG. 4.

Furthermore, the conductive layer 43 can be a gold soldering pad, a copper foil, a carbon skin, and the combinations thereof, but is not limited thereby. The purpose of the conductive layer 43 is to enable each contact layer 42 to connect electrically to the signal processing module 41 and thus enable the bio signals to be transmitted to the signal processing module 41 smoothly. Thus, as each contact layer of the present embodiment can be formed directly upon the conductive layer 43, the overall thickness of the bio-monitoring apparatus 4 can be reduced while the amount of electrically connections required to be enabled inside the bio-monitoring apparatus between the components thereof are also reduced.

To sum up, the bio-monitoring apparatus is advantageous in that: it is a comparatively thinner structure as the amount of electrically connections required to be enabled inside the bio-monitoring apparatus between the components thereof are reduced, by which not only the path of signal transmission is shortened, but also the comfort of a being as one is being monitored thereby is improved.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A bio-monitoring apparatus, comprising:
   a signal processing module;
   at least one electrode patch, each disposed on the signal processing module while being enabled to sensing a bio signal, wherein the electrode patch further comprises an electrode, having a via hole formed thereon; and at least one contact layer, capable of connecting electrically to at least one conductive layer though the via hole, and the electrode is an object selected from the group consisting of a self-adhesive conductive paste, a silicon rubber conductive sheet, an aluminum conductive sheet and the combinations thereof; and
   the at least one conductive layer, each being formed and sandwiched between the at least one electrode patch and the signal processing module for enabling an electrical connection between the at least one electrode patch and the signal processing module and thus enabling the bio signal to be transmitted to the signal processing module.

2. The bio-monitoring apparatus of claim 1, wherein of the at least one contact layer is made of a material selected from the group consisting of a conductive adhesive, a conductive paste and the combinations thereof.

3. The bio-monitoring apparatus of claim 1, wherein a layer of a conductive material is further formed on the electrode at a position sandwiched between the contact layer and the electrode and is electrically connected to the at least one contact layer and the conductive layer.

4. The bio-monitoring apparatus of claim 3, wherein the conductive material is a material selected from the group consisting of a conductive adhesive, a conductive paste and the combinations thereof.

5. The bio-monitoring apparatus of claim 1, wherein the conductive layer is made of a material selected from the group consisting of a gold soldering pad, a copper foil, a carbon skin, and the combinations thereof.

6. The bio-monitoring apparatus of claim 1, wherein the signal processing module further comprises:
   a flexible substrate; and
   at least a processing circuit, formed on the flexible substrate for processing the bio signal.

7. The bio-monitoring apparatus of claim 1, further comprising:
   a power module, for providing power to the signal processing module.

* * * * *